(12) United States Patent
Derr

(10) Patent No.: US 6,929,615 B2
(45) Date of Patent: Aug. 16, 2005

(54) EROGONOMIC COMPUTER WRIST WRAP

(76) Inventor: Terrance Lee Derr, 9988 Windmill Lakes Apt 1805, Houston, TX (US) 77075

( * ) Notice: Subject to any disclaimer, the term of this patent is extended or adjusted under 35 U.S.C. 154(b) by 39 days.

(21) Appl. No.: 10/298,911

(22) Filed: Nov. 19, 2002

(65) Prior Publication Data

US 2004/0097858 A1 May 20, 2004

(51) Int. Cl.$^7$ ................................................ A61F 5/00
(52) U.S. Cl. .......................... 602/20; 602/21; 128/878; 128/879; 248/118
(58) Field of Search ................................ 128/846, 878, 128/879, 882; 602/20, 21; 248/118, 118.1, 118.5

(56) References Cited

U.S. PATENT DOCUMENTS

| | | | |
|---|---|---|---|
| 3,533,407 A | 10/1970 | Smith | 128/165 |
| 4,883,073 A | 11/1989 | Aziz | 128/878 |
| 5,014,689 A | 5/1991 | Meunchen et al. | 128/77 |
| 5,160,314 A | 11/1992 | Peters | 602/21 |
| 5,439,192 A * | 8/1995 | King | 248/118 |
| 5,466,215 A | 11/1995 | Lair et al. | 602/21 |
| 5,649,900 A | 7/1997 | Kline | 602/21 |
| 5,730,711 A * | 3/1998 | Kendall | 602/21 |
| 5,766,141 A | 6/1998 | Gould | 602/21 |
| 5,769,804 A | 6/1998 | Harris et al. | 602/21 |
| 6,082,682 A * | 7/2000 | So et al. | 248/118 |
| 6,213,969 B1 | 4/2001 | MacMorran et al. | 602/64 |
| 6,383,157 B1 | 5/2002 | Massi et al. | 602/21 |
| 6,592,537 B2 * | 7/2003 | Stager | 128/878 |

* cited by examiner

*Primary Examiner*—Michael A. Brown

(57) ABSTRACT

An ergonomic wrist wrap defined by a flexible elongated material having a first terminal portion, a middle portion, and an opposite terminal portion. Each portion has an external surface and an internal surface. The first terminal portion having a substantially rectangular shape with a first lateral edge and the opposite terminal portion having a substantially rectangular shape with a opposite lateral edge. The middle portion has a substantially square with dimensions to support the heel of a hand. The middle portion have a second lateral edge integrated with the first lateral edge the first terminal portion and a second opposite lateral edge integrated with the second opposite lateral edge of the opposite terminal portion. The present invention further includes a fastener means for holding the wrist wrap in place around the wrist. The fastener means comprises a catch which is securely attach to the exterior surface of the first terminal portion and a mate which is securely attach to the interior surface of the opposite terminal portion. A heel pillow is removably attached to the middle portion and provides support for the wrist during movement.

29 Claims, 4 Drawing Sheets

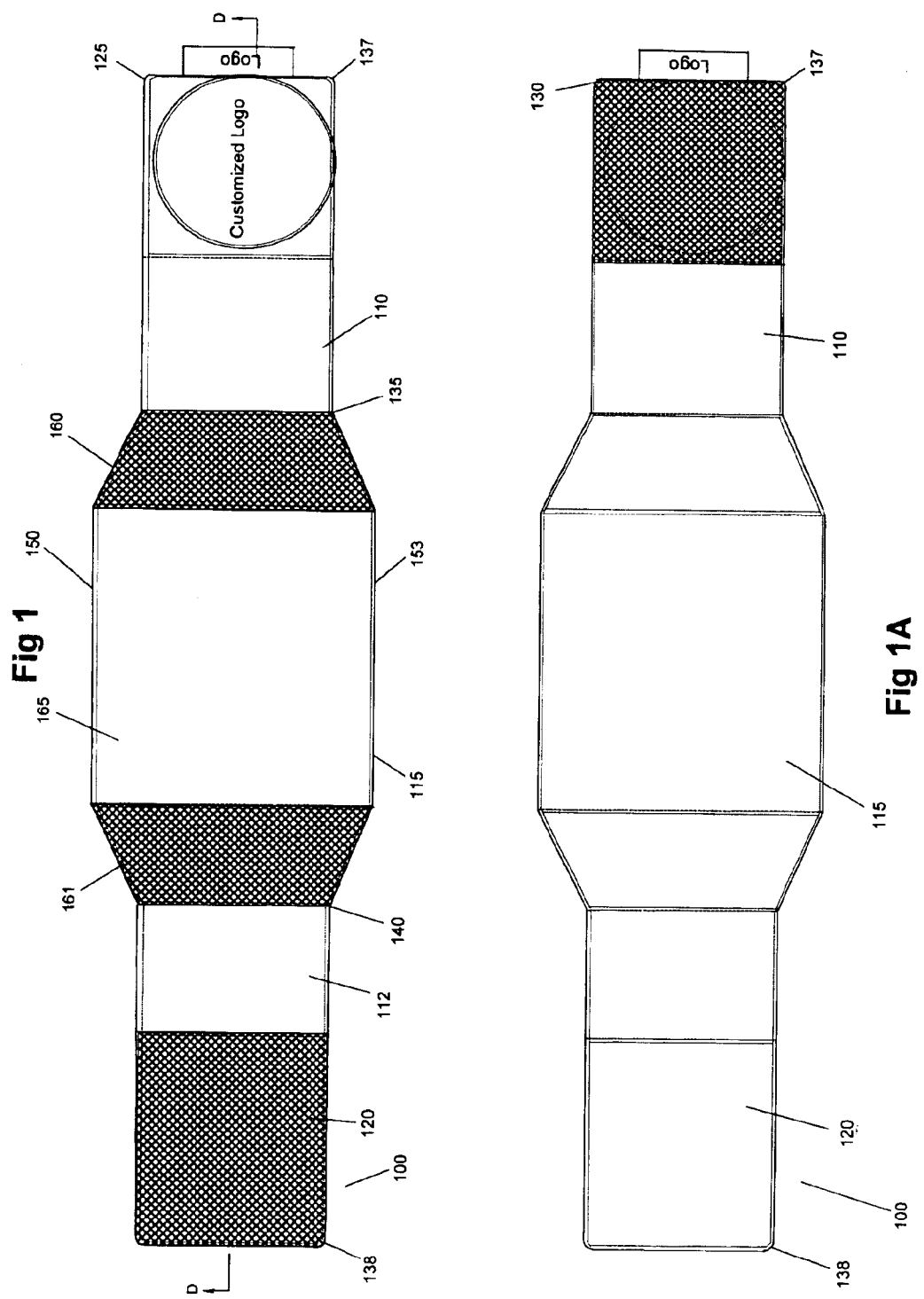

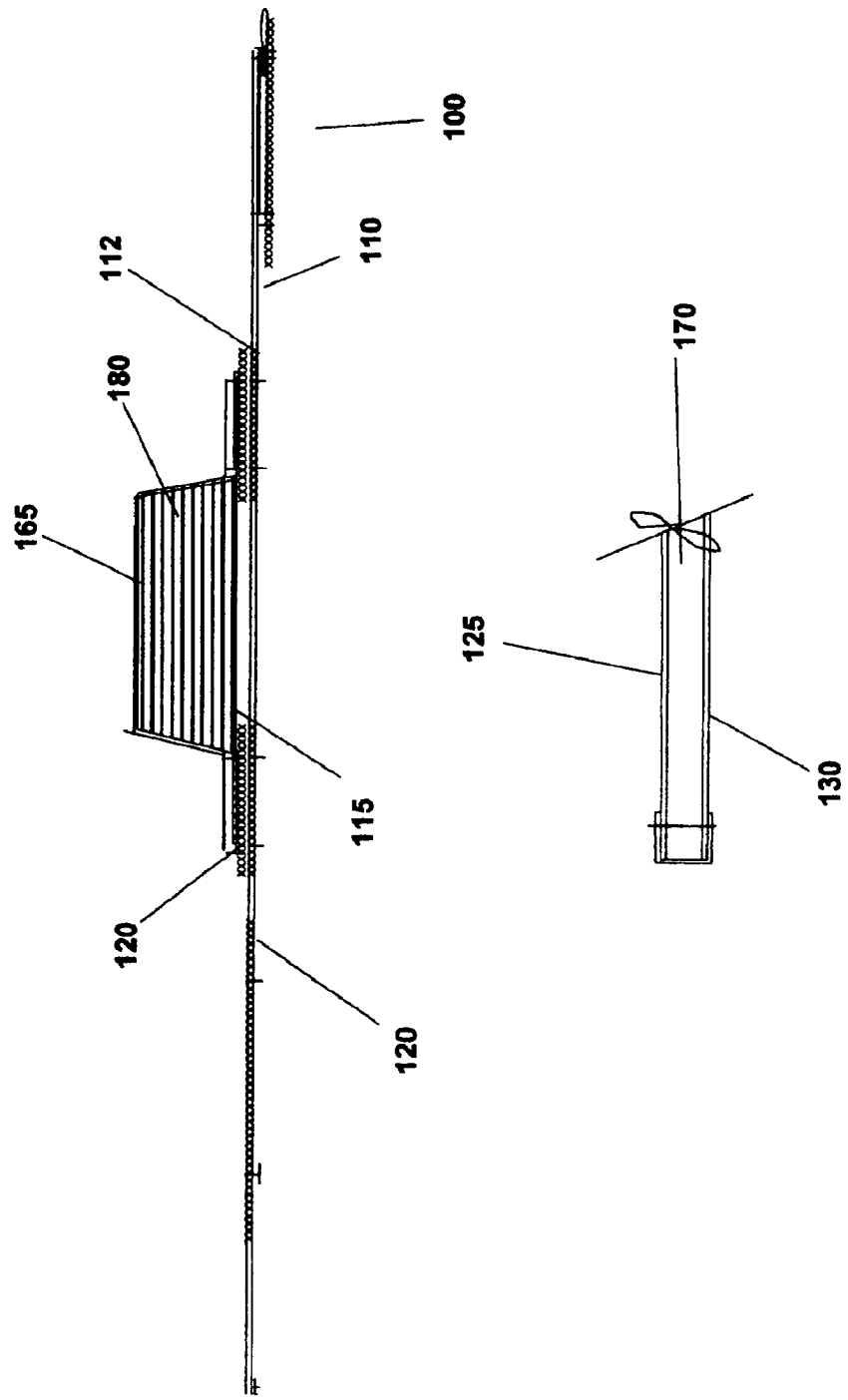

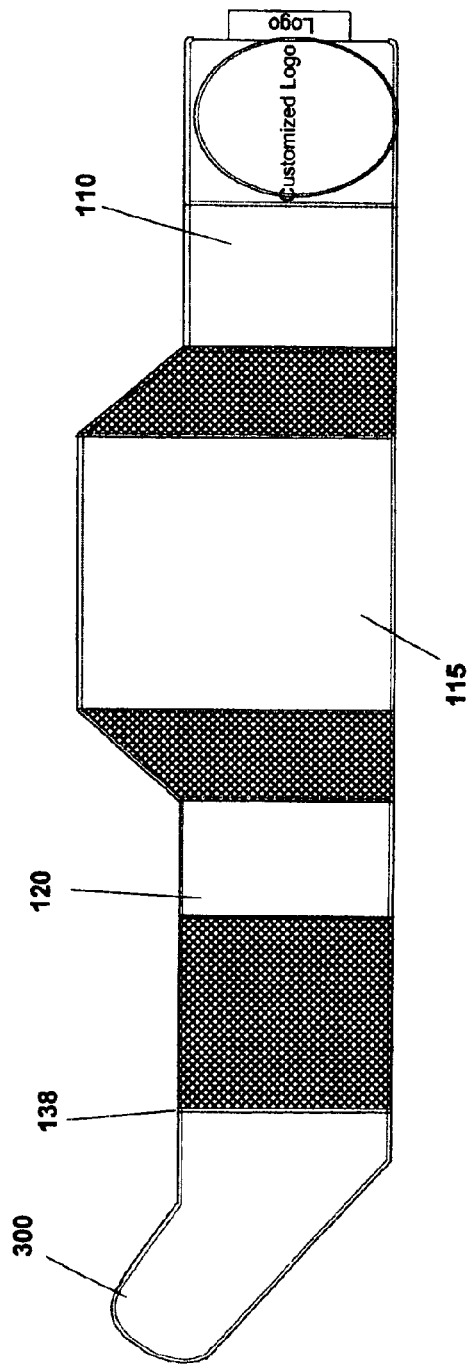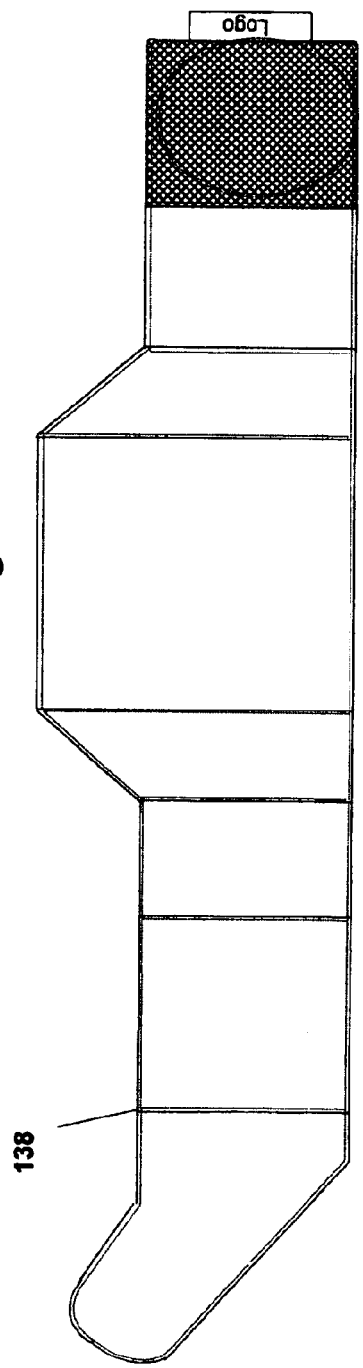

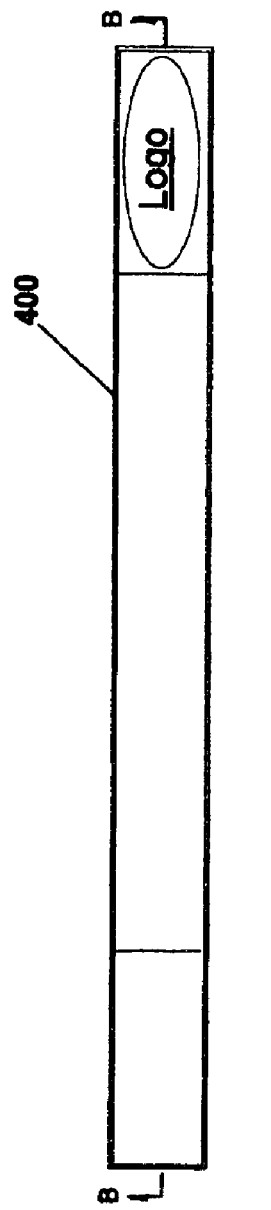
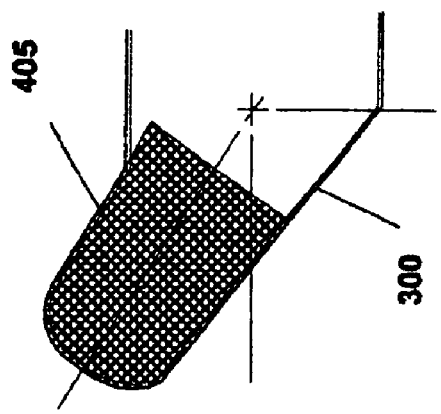
Fig 5
Fig 5A

EROGONOMIC COMPUTER WRIST WRAP

BACKGROUND

This invention relates to ergonomic devices for use with personalized computers, keyboards, and computer mouse. More particularly, the present invention relates to an ergonomic wrist wrap designed to provide personalized comfort for each hand/wrist during day to day use of personalized computers.

Carpel Tunnel Syndrome is a term used to describe a group of symptoms (tingling, numbness, weakness, or pain) in the fingers or hand. Carpal tunnel syndrome occurs when there is swelling or thickening of tissues close to or within the carpal tunnel in the wrist. The swelling or thickening increases pressure on the median nerve and may cause the tingling, numbness, weakness, or pin of carpal tunnel syndrome. Repetitive hand and wrist movements can cause the membranes that surround the tendons to swell.

The prior art provides wrist splints which treat carpal tunnel syndrome after the condition occurs, for example, U.S. Pat. Nos. 5,649,900 and 5,160,314.

Normally, performing repetitive activities, such as typing at the keyboard, that require the wrist to be in an awkward position for a long period of time can increase the chances of getting carpal tunnel syndrome. The best way to prevent carpal tunnel syndrome is to use correct posture while performing these typing activities. The forearm should be kept parallel to the floor or slightly lowered and the wrists should be in line with your arms and not twisted or bent for long periods of time. The present invention helps to prevent carpal tunnel syndrome by keeping the wrist in the correct posture while performing these typing activities.

SUMMARY

The present invention provides an ergonomic wrist wrap to help in the prevention of carpal tunnel syndrome. The present invention includes a flexible elongated material dimensioned to fit around a wearer's wrist and shaped to define a middle portion, a first integral terminal flap, and an opposite integral terminal flap. The elongated material has an external surface and an internal surface wherein can each surface be made of a separate layer of flexible fabric. The outer peripheral edges of each surface are bonded together.

The middle portion further comprises a top, bottom, and two opposing side edges. Extending from one of the opposing side edges is the first integral terminal flap and extending from the second opposing side edge is the opposite integral terminal flap. Situated within the heel pillow is a cushion means which can be made of a dry polymer gel. The heel pillow is dimensioned to fit the wearer's palm region and has dimensions corresponding to the middle portion as well as being removably attached to the external surface of the middle portion.

In order to secure the wrist wrap around the wearer's wrist, a releasable fastener means is cooperatively attached to each terminal flap. When the first and opposite terminal flap are brought together to secure the wrist wrap in place around the wearer's wrist, the heel pillow is secured within the palm region to support the wearer's wrist during movement and to keep the wearer's wrist in correct posture while the wearer of the wrist wrap is performing typing activities.

In alternative embodiments, fanning upward from the opposite terminal lateral edge is a pillow ear for the right hand or fanning upward from the first terminal lateral edge is a pillow for the left hand. In use, the thumb grasps the pillow ear while the wrists wrap is being applied around the wearer's wrist. In other alternative embodiments, a right hand and left hand thumb loop is provided to accommodate the thumb of the wearer of the wrist wrap. The thumb loop is attached at the upper end of the appropriate pillow ear.

BRIEF DESCRIPTION OF DRAWINGS

FIGS. 1 and 1A illustrates a top plan view and a bottom plan view of the preferred embodiment of the present invention.

FIG. 2 illustrates an exploded cross-sectional view of the elongated material of the present invention.

FIG. 3 illustrates a cross-sectional view of the wrist wrap of the present invention.

FIGS. 4 and 4A illustrates a top plan view and a bottom plan view of an alternative embodiment of the present invention.

FIG. 5 illustrates an exploded view of the thumb loop.

FIG. 5A illustrates the pillow ear with releasable fastener means attached to its upper end.

DETAILED SPECIFICATION

Referring to FIGS. 1 and 1A, there is shown a top plan view and a bottom plan view of the preferred embodiment of the present invention, an ergonomic wrist wrap (100) in its opened position. In the illustrated embodiment, the present invention includes a flexible elongated material (112) being defined by a first terminal flap (110), a middle portion (115), and an opposite terminal flap (120). Each portion (110, 115, 120) of the elongated material (112) has an external surface (125) and an interior surface (130).

The elongated material (112) is fabricated into the shape and dimensions required to support its three integrated sections, first terminal flap (110), opposite terminal flap (115) and the middle portion (120). As shown in FIGS. 1 and 1A, the middle portion is further defined by a top (150), a bottom (153), and two integrated opposing sides. As shown in FIG. 1, the first terminal flap (110) has a rectangular shape with three terminal edges and an integrated first lateral edge (135). The first lateral edge (135) of the first terminal flap (110) is integrated with one of the opposing sides of the middle portion (115) and extends outward to a terminal lateral edge (137) of the first terminal flap. Additionally, the opposite terminal flap (120) has a rectangular shape with three terminal edges and an integrated opposite lateral edge (140). The opposite lateral edge (135) of the opposite terminal flap (120) is integrated with the second opposing side of the middle portion (115) and extends outward to a terminal lateral edge (138) of the opposite terminal flap (120). In the embodiment illustrated in FIGS. 1 and 1A, the middle portion (115) has substantially a polygonal shape dimensioned to support the heel of the hand. In the shown embodiment, middle portion (115) is fabricated into an octagonal shape. However, each section of the elongated material (112) can be fabricated into other geometric designs suitable to support the present invention.

The elongated material is made of a flexible material. In one embodiment of the present invention, the elongated material can be made of leather with its outer peripheral edges bonded with a trim. Referring to FIG. 2 there is shown an exploded cross-sectional view of the elongated material. In some embodiments, as shown in FIG. 2 the external surface (125) and internal surface (130) of the elongated material (112) are each made with a separate layer of material. Then, the two surfaces (125, 130) are then bonded together along their outer peripheral edges. In the preferred embodiment of the present invention, each layer of the elongated material is made of a polyester blend type of fabric. In some specific preferred embodiments, by design choice, the two surfaces (125, 130) are securely bonded together along their outer peripheral edges with a stretch polyester bonding. In other specific embodiments, each separate layer can also be made of denim cotton. Additionally, to provide additional support to the wrist wrap, filler (170) can be sandwiched between the internal surface (130) and the internal surface (125) of the elongated material (112). The filler (170) can be made of polyurethane foam.

Referring to FIG. 3 there is shown a cross-sectional view of the wrist wrap (100). The wrist wrap (100) of the present invention further comprises a heel pillow (165) dimensioned to fit the wearer's palm region. The heel pillow (165) is configured to have the same shape and dimensions corresponding to the middle portion (115). Thus, as shown in FIGS. 1 and 1A, corresponding to the shape of the middle portion (115) in the illustrated embodiment, the heel pillow (165) has an octagonal shape with opposing trapezoidal sides (160, 161). Each trapezoidal side (160, 161) of the heel pillow (165) is adapted to be removably attached to its corresponding trapezoidal element on the external surface (125) of the middle portion (115). With the present invention, each trapezoidal side (160, 161) of the heel pillow (165) and its corresponding trapezoidal element of the middle portion (115) are equipped with releasable fastener means. By design choice, the releasable fastener means shown in FIG. 3 is VELCRO. However, the releasable fastener means can be snaps or another such compatible fastener means.

In the illustrated embodiment in FIG. 3, the heel pillow (165) is constructed from the same material as the elongated material (112). Disposed within the heel pillow (165) is a cushion means (180) that allows the heel pillow (165) to adjust to the contour of the wearer's wrist. In the preferred embodiment of the present invention, the cushion means (180) is made from a dry polymer gel. In alternative embodiments, the cushion means (180) can be made of silicone foam, neoprene foam, sponge foam, or other such compatible cushioning material.

Referring again to FIGS. 1 and 1A, the wrist wrap (100) of the present invention further includes an aesthetic pleasing customized flap logo (190) and strap logo (195). In order to make the wrist wrap more aesthetically pleasing to the wearer, a customized flap logo (190) and strap logo (195) that matches the fabric of the elongated material (112) can be applied to the wrist wrap (100). The customized logo flap (190) can be securely bonded to the external surface (125) of the first terminal flap (110), and the strap logo flap (195) can be securely bonded between the internal surface (130) and external surface (125) layers of the terminal lateral edge (137) of the first terminal flap (110). Heat transfer is one mechanism for securely bonding the logos to fabric. Another mechanism for securely bonding the logos is stitching the outer peripheral edges of the logos to the fabric. In addition, the applied customized logos can also be some type of company Trademark.

Another important element of the present invention illustrated in FIGS. 1 and 1A is the releasable fastener means, which includes a mate section (200) and a catch section (210). As shown, the mate section (200) is attached to the internal surface (125) of the first terminal flap (110) and the catch section (210) is attached to the external surface (130) of the opposite terminal flap (120). The wrist wrap is secured in place around the wearer's wrist when the catch section (210) is attached to the mate section (200). When the mate section (200) and the catch section (210) cooperatively attach together, the diameter of the wrist wrap is adjusted to fit the wearer's wrist thereby adjusting the tension of the heel pillow upon the palm region of the wearer's wrist. The fastener means can be VELCRO that is matter of design choice. However, other fastener means such as snaps and hooks and other suitable means can be utilized.

In the present invention, the elongated flexible material is dimensioned to fit the around the wearer's wrist. The dimensions of the entire wrist wrap can be varied to fit the wrist of a small child to the wrist of a large adult. Table 1 below illustrates an example of the dimensions of the preferred embodiment shown in FIGS. 1 and 1A from extra small to extra large.

TABLE 1

|  | First Terminal Flap | Opposite Terminal Flap | Middle Portion | Heel Pillow |
|---|---|---|---|---|
| Extra Small |  |  |  |  |
| Width of side Edge | 2.0 inches | 2.0 inches | 2.0 inches | 2.75 inches |
| Length | 2.5 inches | 2.5 inches | 3.0 inches | 1.5 inches |
| Small |  |  |  |  |
| Width of side Edge | 2.0 inches | 2.0 inches | 2.0 inches | 2.75 inches |
| Length | 2.75 inches | 2.75 inches | 3.25 inches | 1.75 inches |
| Medium |  |  |  |  |
| Width of side Edge | 2.0 inches | 2.0 inches | 2.0 inches | 2.75 inches |
| Length | 3.25 inches | 3.0 inches | 3.5 inches | 2.0 inches |
| Large |  |  |  |  |
| Width | 2.0 inches | 2.0 inches | 2.0 inches | 2.75 inches |
| Length | 3.25 inches | 3.625 inches | 3.875 inches | 2.375 inches |
| Extra Large |  |  |  |  |
| Width of side Edge | 2.0 inches | 2.0 inches | 2.0 inches | 2.75 inches |
| Length | 4.125 inches | 3.5 inches | 4.125 inches | 2.625 inches |

In use, the wrist wrap is placed in an opened position as shown in FIGS. 1 and 1A with the heel pillow lying upon a flat surface. The wearer of the wrist wrap places their hand face down with the heel of the palm lying upon the interior surface of the middle portion. Then, the opposite terminal flap is brought over the top of the wrist. Next, the first terminal flap is brought over the top of the wrist. Finally, the releasable fastener means is securely attached together to secure the wrist wrap in place around the wearer's wrist with the appropriate tension. This structure facilitates the closure of the wrist wrap such that the heel pillow can support the wearer's wrist during movement and can keep the wearer's wrist in correct posture while the wearer of the wrist wrap is performing typing activities. The important aspect of this invention is that an aesthetically pleasing wrist wrap is worn to prophylactically prevent carpal tunnel syndrome.

Referring to FIGS. 4 and 4A, there is shown a top plan view and a bottom plan view for an alternative embodiment for the present invention. In this embodiment, the wrist wrap (100) further comprises an integrated right hand pillow ear (300) which fans upward from the terminal lateral edge (138) of the opposite terminal flap (120). As shown, as the right hand pillow ear (300) fans upward an inner angle is form. By design choice, this angle is thirty degrees.

However, the geometric design of the pillow ear (300) is not limited to a thirty degrees angle. In use, the wearer grasps the pillow ear (300) with their right hand thumb while the wrist wrap is being applied to the wearer's wrist. With the pillow ear (300) firmly held by the thumb, the mate section (200) of the first terminal flap (110) is brought over to attach to the catch section (210) of the opposite terminal flap (120). After the wrist wrap is secured around the wrist of the wearer, the pillow ear is tucked inside at the place of attachment of the flaps. To create this alternative embodiment for the left hand, the configuration is reversed. Here, the pillow ear (300) would fan upward from the terminal lateral edge (137) of the first terminal flap (110). In use, the wrist wrap would function as described above with the left hand thumb. Additionally, for the embodiment illustrated in FIGS. 4 and 4A, the elongated material can be fabricated from leather or from polyester blend multi-layers as described above.

In some alternative embodiments, a thumb loop is attached to the upper end of the pillow ear to accommodate the thumb of the wearer of the wrist. As shown in FIG. 5, the thumb loop (400) is a strip of material dimensioned to accommodate the wearer of the wrist wrap. The loop can be made of the same fabric as the elongated material. In other alternative embodiments, the thumb loop (400) can be releasably attached to the pillow ear (300). As shown in FIG. 5A, to support this configuration, a catch section (405) is situated at the upper end of the pillow ear (300). Attached at the opposing ends of the strip are releasable fastener means (410, 415) which mate with the catch section (405). In use, the thumb loop (400) is placed around the thumb and then secured in place by the releasable fastener means (410, 415). By design choice, the releasable fastener means is VEL-CRO. However, compatible fasteners can be utilized. To create this alternative embodiment for the left hand, the configuration is reversed and the thumb loop is attached the pillow ear fanning off of the terminal lateral edge of the first terminal flap.

What is claimed is:

1. An ergonomic wrist wrap comprising:
   a flexible elongated material dimensioned to fit around a wearer's wrist and shaped to define a middle portion, a first integral terminal flap, and an opposite integral terminal flap, the elongated material having an external surface and an internal surface;
   the middle portion having a top, bottom, and two opposing side edges;
   the first integral terminal flap extending from one opposing side edge to a first terminal lateral edge;
   the opposite integral terminal flap extending from the second opposing side edge to an opposite terminal lateral edge;
   a heel pillow dimensioned to fit the wearer's palm region, the heel pillow having dimensions corresponding to the middle portion and being removably attached to the external surface of the middle portion; and
   a releasable fastener means cooperatively attached to each terminal flap such that the first and opposite terminal flap can be brought together to secure the wrist wrap in place around the wearer's wrist, whereby the heel pillow can support the wearer's wrist during movement and can keep the wearer's wrist in correct posture while the wearer of the wrist wrap is performing typing activities; and
   a right pillow ear integral with the opposite terminal lateral edge or a left hand pillow ear integral with the first terminal lateral edge;
   the right hand pillow ear which fans upward from the opposite terminal lateral edge of the opposite terminal flap such that the right hand thumb grasps the right hand pillow ear while the wrists wrap is wrapped in place around the wrist; and
   the left hand pillow ear which fans upward from the first terminal lateral edge of the first terminal flap such that the left hand thumb grasps the left hand pillow ear while the wrists wrap is wrapped in place around the wrist.

2. The wrist wrap of claim 1 wherein the heel pillow is securely attached to the external surface of the middle portion.

3. The wrist wrap of claim 1 wherein the heel pillow further comprises a cushion means disposed within the heel pillow such that the heel pillow adjusts to the contour of the wearer's wrist.

4. The wrist wrap of claim 3 wherein the cushion means is made of a dry polymer gel.

5. The wrist wrap of claim 3 wherein the cushion means is made of silicone foam.

6. The wrist wrap of claim 3 wherein the cushion means is made of neoprene foam.

7. The wrist wrap of claim 3 wherein the heel cushion means is made of sponge foam.

8. The wrist wrap of claim 1 wherein the elongated material is made of leather with a binding trim along its outer peripheral edges.

9. The wrist wrap of claim 1 wherein the first and the opposite terminal flap are substantially rectangular shape.

10. The wrist wrap of claim 1 wherein the middle portion has a polygonal shape.

11. The wrist wrap of claim 1 further comprising an aesthetic customized flap logo attached to the external surface of the first terminal flap.

12. The wrist wrap of claim 9 further comprising a right hand pillow ear which fans upward from the opposite terminal lateral edge of the opposite terminal flap such that the right hand thumb grasps the pillow ear while the wrists wrap is wrapped in place around the wrist.

13. The wrist wrap of claim 1 further comprising:
   a right hand thumb loop to accommodate the thumb of a person to whom the wrist wrap is applied; and
   the right hand thumb loop being attached to the pillow ear at its upper end.

14. The wrist wrap of claim 13 wherein the right hand thumb loop is removably attached to the pillow ear.

15. The wrist wrap of claim 9 further comprising a left hand pillow ear which fans upward from the first terminal lateral edge of the first terminal flap such that the left hand thumb grasps the pillow ear while the wrists wrap is wrapped in place around the wrist.

16. The wrist wrap of claim 1 further comprising:
   a left hand thumb loop to accommodate the thumb of a person to whom the wrist wrap is applied; and
   the left hand thumb loop being attached to the pillow ear at its upper end.

17. The wrist wrap of claim 13 wherein the left hand thumb loop is removably attached to the pillow ear.

18. The wrist wrap of claim 1 wherein the external surface and internal surface are each made with a separate layer of material securely bonded together along their outer peripheral edges.

19. The wrist wrap of claim 18 further comprising an aesthetic strap logo attached to the terminal lateral edge of the first terminal flap between the external surface layer of material and internal surface layer of material.

20. The wrist wrap of claim 18 wherein each layer of material is made of denim cotton.

21. The wrist wrap of claim 18 wherein each layer of material is made of a polyester blend.

22. The wrist wrap of claim 18 further comprising filler sandwiched between the internal face and the external face.

23. The wrist wrap of claim 1 wherein the releasable fastener means cooperate to adjust the diameter of the wrist wrap to fit the wearer's wrist thereby adjusting the tension of the heel pillow upon the palm region of the wearer's wrist.

24. An ergonomic wrist wrap further comprising:
a flexible elongated material dimensioned to fit around a wearer's wrist and shaped to define a middle portion, a first integral terminal flap, and an opposite integral terminal flap, the elongated material having an external surface and an internal surface, the external surface and internal surface being made of a separate layer of flexible fabric;
the middle portion having a top, bottom, and two opposing side edges; the first integral terminal flap extending from one opposing side edge to a first terminal lateral edge;
the opposite integral terminal flap extending from the second opposing side edge to an opposite terminal lateral edge;
a pillow ear fanning upward from the opposite terminal lateral edge for the right hand or fanning upward from the first terminal lateral edge for the left hand wherein the thumb grasps the pillow ear while the wrists wrap is being applied around the wearer's wrist;
a heel pillow having a cushion means made of a dry polymer gel, the heel pillow being dimensioned to fit the wearer's palm region and having dimensions corresponding to the middle portion, and the heel pillow being removably attached to the external surface of the middle portion; and
a releasable fastener means cooperatively attached to each terminal flap such that the first and opposite terminal flap can be brought together to secure the wrist wrap in place around the wearer's wrist, whereby the heel pillow can support the wearer's wrist during movement and can keep the wearer's wrist in correct posture while the wearer of the wrist wrap is performing typing activities.

25. An ergonomic wrist wrap further comprising:
a flexible elongated material dimensioned to fit around a wearer's wrist and shaped to define a middle portion, a first integral terminal flap, and an opposite integral terminal flap, the elongated material having an external surface and an internal surface, the external surface and internal surface being made of a separate layer of flexible fabric;
the middle portion having a top, bottom, and two opposing side edges;
the first integral terminal flap extending from one opposing side edge to a first terminal lateral edge;
the opposite integral terminal flap extending from the second opposing side edge to an opposite terminal lateral edge;
the first terminal lateral edge inclining upward to a top edge of the first opposing side edge of the middle portion;
the opposite terminal lateral edge inclining upward to a top edge of the second side of the middle portion;
a heel pillow having a cushion means made of a dry polymer gel, the heel pillow being dimensioned to fit the wearer's palm region and having dimensions corresponding to the middle portion, and the heel pillow being attached to the external surface of the middle portion; and
a releasable fastener means cooperatively attached to each terminal flap such that the first and opposite terminal flap can be brought together to secure the wrist wrap in place around the wearer's wrist, whereby the heel pillow can support the wearer's wrist during movement and can keep the wearer's wrist in correct posture while the wearer of the wrist wrap is performing typing activities.

26. An ergonomic wrist wrap further comprising:
a flexible elongated material dimensioned to fit around a wearer's wrist and shaped to define a middle portion, a first integral terminal flap, and an opposite integral terminal flap, the elongated material having an external surface and an internal surface, the external surface and internal surface being made of a separate layer of flexible fabric;
the middle portion having a top, bottom, and two opposing side edges;
the first integral terminal flap extending from one opposing side edge to a first terminal lateral edge;
the opposite integral terminal flap extending from the second opposing side edge to an opposite terminal lateral edge;
a pillow ear fanning upward from the opposite terminal lateral edge for the right hand or fanning upward from the first terminal lateral edge for the left hand wherein the thumb grasps the pillow ear while the wrists wrap is being applied around the wearer's wrist;
a thumb loop attached to the pillow ear at its upper end;
a heel pillow having a cushion means made of a dry polymer gel, the heel pillow being dimensioned to fit the wearer's palm region and having dimensions corresponding to the middle portion, and the heel pillow being removably attached to the external surface of the middle portion; and
a releasable fastener means cooperatively attached to each terminal flap such that the first and opposite terminal flap can be brought together to secure the wrist wrap in place around the wearer's wrist, whereby the heel pillow can support the wearer's wrist during movement and can keep the wearer's wrist in correct posture while the wearer of the wrist wrap is performing typing activities.

27. An ergonomic wrist wrap comprising:
a flexible elongated material dimensioned to fit around a wearer's wrist and shaped to define a middle portion, a first integral terminal flap, and an opposite integral terminal flap, the elongated material having an external surface and an internal surface;
the middle portion having a top, bottom, and two opposing side edges;
the first integral terminal flap extending from one opposing side edge to a first terminal lateral edge;
the opposite integral terminal flap extending from the second opposing side edge to an opposite terminal lateral edge;
the first terminal lateral edge inclining upward to a top edge of the first opposing side edge of the middle portion;
the opposite terminal lateral edge inclining upward to a top edge of the second side edge of the middle portion;

a heel pillow dimensioned to fit the wearer's palm region, the heel pillow having dimensions corresponding to the middle portion and being attached to the external surface of the middle portion;

a realeasable fastener means cooperatively attached to each terminal flap such that the first and opposite terminal flap can be brought together to secure the wrist wrap in place around the wearer's wrist, whereby the heel pillow can support the wearer's wrist during movement and can keep the wearer's wrist in correct posture while the wearer of the wrist wrap is performing typing activities.

28. The wrist wrap of claim 27 wherein the cushion means is made of a dry polymer gel.

29. The wrist wrap of claim 27 wherein the heel pillow is removably attached to the external surface of the middle portion.

* * * * *